United States Patent
Neis et al.

(10) Patent No.: US 7,431,949 B2
(45) Date of Patent: Oct. 7, 2008

(54) TOPICAL COSMETIC COMPOSITIONS CONTAINING ALPHA ARBUTIN

(75) Inventors: Arnold Neis, New York, NY (US); Robert Neis, New York, NY (US); Jerry Whittemore, Los Angeles, CA (US)

(73) Assignee: E.T. Browne Drug Co., Inc., Engelwood Cliffs, NJ (US)

( * ) Notice: Subject to any disclaimer, the term of this patent is extended or adjusted under 35 U.S.C. 154(b) by 0 days.

(21) Appl. No.: 11/745,632

(22) Filed: May 8, 2007

(65) Prior Publication Data

US 2007/0207110 A1    Sep. 6, 2007

Related U.S. Application Data

(62) Division of application No. 11/060,348, filed on Feb. 18, 2005, now abandoned.

(51) Int. Cl.
A01N 65/00 (2006.01)
(52) U.S. Cl. .................................................. 424/725
(58) Field of Classification Search ............... None
See application file for complete search history.

(56) References Cited

U.S. PATENT DOCUMENTS

| | | | |
|---|---|---|---|
| 4,278,656 A | | 7/1981 | Nagai et al. |
| 4,764,505 A | | 8/1988 | Fujinuma et al. |
| 5,234,682 A | * | 8/1993 | Macchio et al. ............. 424/69 |
| 5,310,730 A | | 5/1994 | Fujinuma et al. |
| 5,389,363 A | * | 2/1995 | Snyder et al. .............. 424/70.7 |
| 5,700,784 A | | 12/1997 | Shinujima et al. |
| 5,747,006 A | | 5/1998 | Dornoff et al. |
| 5,824,327 A | | 10/1998 | Whittemore et al. |
| 5,932,608 A | | 8/1999 | Nguyen et al. |
| 5,980,904 A | | 11/1999 | Ley et al. |
| 6,068,847 A | * | 5/2000 | Aleles et al. ................ 424/401 |
| 6,077,503 A | | 6/2000 | Dornoff et al. |
| 6,395,260 B1 | | 5/2002 | Ley et al. |
| 6,492,326 B1 | | 12/2002 | Robinson et al. |
| 6,537,527 B1 | | 3/2003 | Kvalnes et al. |
| 6,790,452 B2 | * | 9/2004 | Kishida et al. .............. 424/401 |
| 2005/0147631 A1 | * | 7/2005 | Goldstein et al. ........... 424/401 |
| 2006/0165620 A1 | * | 7/2006 | Bujard et al. ................ 424/63 |

FOREIGN PATENT DOCUMENTS

EP    0672746    9/1995

OTHER PUBLICATIONS

"Melanins and Melanogenesis", Giuseppe Prota, Ph.D., Cosmetics and Toiletries, vol. 111, May 1996.
"Dermawhite," Laboratoires Serobiologiques, Division de Cognis, France.
"Textbook of Pharmacognosy," Heber W. Youngken, p. 639, Blakiston, Philadelphia, 1948.
"Rodale's Illustrated Encylopedia of Herbs," pp. 163-172, Rodale Press, Emmanaus, PA 1997.
"Reduced skin irritation with tretinoin containing polyolprepolymer-2, a new topical tretinoin delivery system: A summary of preclinical and clinical investigations," pp. S5-S10, 1998, Supported by an Educational Grant From Penederm Inc.

* cited by examiner

*Primary Examiner*—Michael V Meller
(74) *Attorney, Agent, or Firm*—Barbara A. Wrigley; Oppenheimer Wolff & Donnelly LLP

(57) ABSTRACT

This invention is a topical tyrosinase inhibiting combination using alpha arbutin and bearberry extract, in synergism, for the purpose of skin lightening. The active admixture is a dermatological serum comprised of alpha arbutin, octyl stearate and polyolprepolymer-2, introduced onto the human skin in liposome form for ultra-deep penetration.

16 Claims, No Drawings

TOPICAL COSMETIC COMPOSITIONS CONTAINING ALPHA ARBUTIN

CROSS REFERENCE TO RELATED APPLICATIONS

This application is a divisional application of application Ser. No. 11/060,348, filed Feb. 18, 2005, and entitled "TOPICAL COSMETIC COMPOSITIONS CONTAINING ALPHA ARBUTIN."

FIELD OF THE INVENTION

The invention relates to topical cosmetic compositions, in particular, human skin lightening compositions, comprising admixtures of alpha arbutin and bearberry extract used for topical application.

BACKGROUND OF THE INVENTION

The present invention is a novel topically applied dermo-cosmetic composition comprising certain admixtures of the glucoside alpha arbutin and the botanical extract bearberry to be used in skin lightening.

Certain humans at different phases of their lifetime, and from different parts of the world, and in differing phases of their health develop excess melanin and/or colored blemishes on the skin. This excess melanin can occur on any part of the human body, but most commonly appear on the face and back of the hands. These dark spots are caused by high levels of melanin in the keratinocytes located in the top layer of the epidermis.

Melanocytes are located deep in the stratum granulosum, produce melanin, and through an unknown mechanism the melanin rises through about 100 cell layers to the surface where they exist as unsightly dark spots.

Biochemically, the process is:

Tyrosine amino acid (from diet) goes to Dopa; Dopa goes to Dopaquinone; Dopaquinone goes to Dopachrome; Dopachrome goes to Melanin.

Melanin deposits are seen as the dark spots on the surface of the human skin. They may be called "sun spots" or "age spots" or "liver spots."

Tyrosinase Inhibition

Tyrosinase is the enzyme which catalyzes the amino acid tyrosine into dopa (dihydroxyphenylamine), as well as the change from dopa into dopaquinone. Skin lightening products are designed to inhibit the action of tyrosinase.

Hydroquinone is the most common inhibitor of the enzyme tyrosinase. Hydroquinone is OTC Monographed (United States Food and Drug Administration 21 CPR) as a Category I skin lightener/skin bleacher/skin whitener in the concentration limits of 1.5-2.0% by weight. Used in this concentration, no clinical trials and no pre-market clearance are necessary in the USA marketplace. Used in higher concentrations than 2% by weight, hydroquinone compositions legally require a prescription in the USA marketplace. Production of hydroquinone preparations over 2% by weight requires an approved ANDA (Approved New Drug Application-21 CFR 394). However, hydroquinone is an irritant to some individuals, particularly those with light skin types, and may be cytotoxic to melanocytes. It is not legally marketed in Japan, the Union of South Africa and several other countries at present, and several other countries are considering denying legal marketing clearance because of concern about long term toxicity.

DETAILED DESCRIPTION OF THE INVENTION

Alpha arbutin avoids the direct toxicity of hydroquinone and the indirect toxicity of beta arbutin which easily hydrolyses to hydroquinone. Alpha arbutin acts more slowly than hydroquinone, taking a slightly longer time to meet the customer's skin lightening objectives when used alone. This invention involves the use of alpha arbutin and bearberry extract in combination. This combination is synergistic in skin whitening effectiveness, as the bearberry extract serves to potentiate the alpha arbutin. Moreover, the alpha-glucosidic bond has a higher stability than the beta glucosidic bond, giving greater stability and greater effectiveness than beta arbutin.

Advanced Liposome Delivery System

This patent teaches that the use of POLYOLPREPOLYMER-2, which is generically known as poly[oxy(methyl-1,2-ethanediyl)], .alpha.-hydro-.omega.-hydroxy-polymer with 1,1'methylene-bis-[4,isocyanatocyclohexane] in an admixture with alpha arbutin/bearberry extract. This is in order to both extend the stability of the alpha arbutin to avoid possible deleterious effects due to oxidation related to the oxygen in the atmosphere as well as that caused by cell respiration potentiators found in epiderinal respiration.

This invention teaches that the use of POLYOLPREPOLYMER-2, when admixed with the serum comprised of alpha arbutin and octyl stearate, can be administered into the human skin using a liposome advanced delivery mechanism. Liposomes can easily be formed by those familiar in the art of liposome manufacture, using either preformed empty liposomes (Brookosomes MT) or by using ultra high pressure (20,000-40,000 PSI) in the usual microfluidizer.

SUMMARY OF THE INVENTION

In the preferred embodiment of this invention, a serum comprised of alpha arbutin 0.01-6.0% w/w (more preferably 1-4% w/w) plus bearberry extract 0.01% w/w (most preferably 1-3% w/w) is admixed with POLYOLPREPOLYMER-2 0.5-10% w/w (most preferably 1-3% w/w), and this combination is further prepared into a liposome form with the use of lecithin, water and ultra high pressure microfluidizer. The liposome formation is well known to those familiar in the use of the ultra high PSI providing microfluidizer.

This invention additionally teaches the serum-liposome admixture being further admixed into a gel or cream carrier as an advanced delivery system used in cosmetic, esthetician, spa and dermatology office settings.

Additionally, this stabilized alpha arbutin-POLYOLPREPOLYMER-liposome concentrate, which has been diluted into a cosmetic carrier, is potentiated with the admixture of the proven botanical extract, bearberry extract. Moreover, additional nutrients including Vitamins A, B, C, E and Panthenol may be included in the liposome addition process.

Clinical testing using before and after microscopic videos establishes that this potentiation takes place in clinical, human usage.

Composition

The most preferable embodiment composition is as follows:

| Part | Ingredient INCI | Percentage by weight |
|---|---|---|
| A | Aqua (water) | qs 100% |
| A | Methylparaben | 0.23 |

-continued

| Part | Ingredient INCI | Percentage by weight |
|------|-----------------|----------------------|
| A | Glycerin | 4 |
| A | EDTA disodium | 0.12 |
| B | Cetearyl alcohol, ceteareth 20 | 9 |
| B | Propylparaben | 0.12 |
| B | Cetyl palmitate | 2 |
| B | Dimethicone 50 (Dimethylpolysiloxane) | 1 |
| B | Steareth-20 (Polyethylene glycol ether of stearyl alcohol) | 1 |
| C | Alpha arbutin | 3 |
| C | Octyl stearate | 7 |
| C | Polyolprepolymer-2 | 2 |
| D | Lecithin, Water (Brookosomes MT) | 1 |
|   | Lecithin, Vitamins A, C & E | 1 |
| E | Bearberry Extract (Gatulin-Gattefosse) | 1 |

Manufacturing Procedure

Manufacturing procedure for the most preferred embodiment is as follows:

The hot part B (80 degrees C.) is mixed into the hot part A (80 degrees C.) to form the conventional emulsion core. Continue mixing and cooling.

Part C is prepared in a separate jacketed kettle at about 45 degrees C.

As part AB is mixing and cooling to about 45 degrees C., slowly add part C with mixing, then slowly add part D (all liposomes).

Continue to mix and cool part ABCD to about 35 degrees C. Slowly add with high agitation the Part E. Continue to mix and cool to 25 degrees C.

What is claimed is:

1. A method for preparing a cosmetic composition comprising:
   preparing a first cosmetic composition component comprising water, methylparaben, glycerin and EDTA disodium;
   heating said first cosmetic composition component to 80 degrees Celsius;
   preparing a second cosmetic composition component comprising cetearyl alcohol, propylparaben, cetyl palmitate, dimethylpolysiloxane and polyethylene glycol ether of stearyl alcohol and heating said second cosmetic composition component to 80 degrees Celsius;
   preparing an emulsion by mixing said second cosmetic composition component with said first cosmetic composition component;
   preparing a third cosmetic composition component comprising alpha arbutin, octyl stearate and poly[oxy(methyl-1,2-ethanediyl)], .alpha.-hydro-.omega.-hydroxy-polymer with 1,1'methylene-bis-[4, isocyanatocyclohexane], wherein said third cosmetic composition component is prepared at 45 degrees Celsius;
   mixing and cooling said emulsion to 45 degrees Celsius;
   mixing said third cosmetic composition component with said emulsion as said emulsion is being cooled to 45 degrees Celsius;
   preparing a non-final cosmetic composition mixture by adding a fourth cosmetic composition component comprising lecithin, water, Vitamin A, Vitamin C, and Vitamin E to the mixture of said third cosmetic composition component and said emulsion;
   cooling said non-final cosmetic composition mixture to 35 degrees Celsius;
   adding bearberry extract to said non-final cosmetic composition mixture to form said cosmetic composition while increasing agitation; and
   cooling said cosmetic composition to 25 degrees while continuously mixing.

2. The method of claim 1 wherein said first cosmetic composition comprises 0.23 wt % methylparaben.

3. The method of claim 1 wherein said first cosmetic composition comprises 4 wt % glycerin.

4. The method of claim 1 wherein said first cosmetic composition comprises 0.12 wt % EDTA disodium.

5. The method of claim 1 wherein said second cosmetic composition component comprises 9 wt % cetearyl alcohol.

6. The method of claim 1 wherein said second cosmetic composition component comprises 0.12 wt % propylparaben.

7. The method of claim 1 wherein said second cosmetic composition component comprises 2 wt % cetyl palmitate.

8. The method of claim 1 wherein said second cosmetic composition component comprises 1 wt % dimethylpolysiloxane.

9. The method of claim 1 wherein said second cosmetic composition component comprises 1 wt % polyethylene glycol ether of stearyl alcohol.

10. The method of claim 1 wherein said third cosmetic composition component comprises 3 wt % alpha arbutin.

11. The method of claim 1 wherein said third cosmetic composition component comprises 7 wt % octyl stearate.

12. The method of claim 1 wherein said third cosmetic composition component comprises 2 wt % poly[oxy(methyl-1,2-ethanediyl)], .alpha.-hydro-.omega.-hydroxy-polymer with 1,1'methylene-bis-[4,isocyanatocyclohexane].

13. The method of claim 1 wherein said fourth cosmetic composition component comprises 1 wt % of a mixture consisting of water and lecithin.

14. The method of claim 1 wherein said fourth cosmetic composition component comprises 1 wt % of a mixture consisting of lecithin, vitamin A, vitamin C and vitamin E.

15. The method of claim 1 said step for adding bearberry extract to said non-final cosmetic composition mixture to form said cosmetic composition while increasing agitation further comprises adding 1 wt % bearberry extract.

16. The method of claim 1 wherein said first cosmetic composition component comprises 67.53 wt % water.

* * * * *